United States Patent
Yamamoto et al.

(10) Patent No.: US 9,579,174 B2
(45) Date of Patent: Feb. 28, 2017

(54) FLOW-TYPE ULTRASONIC ORAL CAVITY WASHING DEVICE

(75) Inventors: Matsuo Yamamoto, Tokyo (JP); Takashi Takiguchi, Tokyo (JP); Masanori Sato, Aichi (JP); Kengo Uemura, Aichi (JP); Tomomi Hikida, Aichi (JP); Katsuyuki Inagaki, Aichi (JP); Hideo Kozaka, Aichi (JP); Toshiaki Miyamoto, Aichi (JP)

(73) Assignees: SHOWA UNIVERSITY, Tokyo (JP); HONDA ELECTRONICS CO., LTD., Aichi (JP); GC CORPORATION, Tokyo (JP)

( * ) Notice: Subject to any disclaimer, the term of this patent is extended or adjusted under 35 U.S.C. 154(b) by 391 days.

(21) Appl. No.: 14/233,209

(22) PCT Filed: Jul. 11, 2012

(86) PCT No.: PCT/JP2012/068263
§ 371 (c)(1),
(2), (4) Date: Jan. 16, 2014

(87) PCT Pub. No.: WO2013/012021
PCT Pub. Date: Jan. 24, 2013

(65) Prior Publication Data
US 2014/0147804 A1    May 29, 2014

(30) Foreign Application Priority Data
Jul. 19, 2011   (JP) ................................ 2011-157519

(51) Int. Cl.
*A61C 17/02*   (2006.01)
*A61C 17/20*   (2006.01)
(Continued)

(52) U.S. Cl.
CPC ............ *A61C 17/20* (2013.01); *A61C 1/0061* (2013.01); *A61C 1/07* (2013.01); *A61C 1/088* (2013.01);
(Continued)

(58) Field of Classification Search
CPC .......... A61C 17/20; A61C 1/07; A61C 1/088; A61C 17/0208; A61C 1/0061; A61C 17/0202
See application file for complete search history.

(56) References Cited

U.S. PATENT DOCUMENTS 5,013,241 A    5/1991  Von Gutfeld et al.
8,398,399 B2 *  3/2013  Paschke ............... A61C 15/047
                                                433/119
(Continued)

FOREIGN PATENT DOCUMENTS

CN    2217389        1/1996
EP    1 600 088     11/2005
(Continued)

*Primary Examiner* — Quang D Thanh
(74) *Attorney, Agent, or Firm* — Clark & Brody

(57) ABSTRACT

This invention is achieved to provide a water-flow ultrasonic oral-cavity cleaning device. In the water-flow ultrasonic oral-cavity cleaning device (1), cleaning liquid (W1) from a cleaning-liquid supplying device (2) is supplied into a transducer case (21) through a supply port (26). Ultrasonic waves (S1) are propagated into the cleaning liquid W1 from an ultrasonic transducer (22) mounted in a transducer mounting part (23) inside the transducer case (21). The water-flow of the cleaning liquid (W1) is collected at the apical-part inside the transducer case (21), and then emitted from the issue (27) into the oral cavity, wherein power supply of 100W or less is supplied to the ultrasonic transducer (22) of 50 mm or less in diameter to propagate the (Continued)

ultrasonic waves (S1) of 100 kHz or more to 3 MHz or less in frequency into the cleaning liquid (W1).

12 Claims, 10 Drawing Sheets

(51) Int. Cl.
  *A61C 1/00* (2006.01)
  *A61C 1/08* (2006.01)
  *A61C 1/07* (2006.01)
(52) U.S. Cl.
  CPC ...... *A61C 17/0202* (2013.01); *A61C 17/0208* (2013.01)

(56) References Cited

U.S. PATENT DOCUMENTS

2006/0234185 A1* 10/2006 Ziemba .................. A61C 1/088
  433/119
2007/0148615 A1* 6/2007 Pond .................... A61C 1/0084
  433/80

FOREIGN PATENT DOCUMENTS

| | | |
|---|---|---|
| JP | 5-171666 | 7/1993 |
| JP | 08-308859 | 11/1996 |
| JP | 11-318917 | 11/1999 |
| JP | 2005-177253 | 7/2005 |
| JP | 2009-131339 | 6/2009 |
| JP | 2009-136648 | 6/2009 |
| WO | 2006/001224 | 1/2006 |
| WO | 2009/047670 | 4/2009 |

\* cited by examiner

FLOW-TYPE ULTRASONIC ORAL CAVITY WASHING DEVICE

TECHNICAL FIELD

This invention relates to a water-flow ultrasonic oral-cavity cleaning device for ultrasonically cleaning the surface of the teeth, of a dental implant, of microorganisms on the oral mucosa, of food residue or the like and to a method of water-flow ultrasonic oral-cavity cleaning.

TECHNICAL BACKGROUND

In the past, high-pressure water-flow devices for cleaning oral cavities have been put into practical use for dental treatment. In the case of using such a device, a large volume of cleaning liquid is needed. Also, during the dental treatment, it is necessary to discharge the cleaning liquid from the mouth of the patient. However, the more liquid that is used, the more processing power for the water-removal device is required, thus making it costly to process the cleaning liquid and drainage.

As a dental treatment, the use of ultrasonic scalers for removing plaque or the like and ultrasonic cleaning-devices for cleaning oral cavities, such as ultrasonic toothbrushes, which devices use ultrasonic vibration, have already been put into practical use. Also, although it is now disclosed as a means for dental treatment, ultrasonic foreign-body removal devices for removing foreign matter by using ultrasonic vibration are suggested (for example, see Patent Document 1, below). Patent Document 1 shows an ultrasonic foreign-body removal device of which the ultrasonic vibration from the oscillator is transmitted to a horn, and foreign matter is removed by the apical end of the horn. This device also has a means for supplying the cleaning liquid to wash out the foreign matter and a means for vacuuming up the foreign matter as well as the cleaning liquid. It is thus possible to clean an oral cavity by using such an ultrasonic foreign-body removal device.

Using the aforementioned ultrasonic scalers, ultrasonic toothbrushes, ultrasonic foreign-body removal devices or the like to clean oral cavities makes it possible to reduce the volume of cleaning liquid being used.

PRIOR ART DOCUMENT

Patent Document 1: JP-A-H11-318917

SUMMARY OF THE INVENTION

Problems to be Solved by the Invention

In fact, a conventional oral-cavity cleaning device, using ultrasonic vibration, allows for plaque to be broken and removed by applying the oscillatory member (chip, the tips of the bristles of a toothbrush, horn, or the like) directly upon the teeth. For a user to manage such an oral-cavity cleaning device, some substantial technique in use (operational proficiency) is required. In other words, since the plaque cannot be removed unless the oscillatory member of a conventional device is surely applied to the plaque, it takes some time to remove the plaque, and sometimes the plaque is insufficiently removed. Thus, it is preferable to use a cleaning device that efficiently and completely provides for the cleaning of an oral cavity regardless of the user's technique.

In a field other than dental treatment, the water-flow ultrasonic cleaning device is now put to practical use. The water-flow ultrasonic cleaning device incorporates an ultrasonic transducer within a case, from which ultrasonic waves are transmitted to a cleaning liquid. The ultrasonic-wave transmission-cleaning liquid-flow is emitted from an outlet nozzle to clean an object such as a semiconductor substrate or the like. This water-flow ultrasonic cleaning device applies comparatively high-frequency waves (i.e. of several megahertz) that remove fine dirt attached to a semiconductor substrate. However, the high-frequency ultrasonic waves of this cleaning device change sharply in direction, so that said waves near the outlet port of the injection nozzle converge narrowly within a comparatively small range. Thus, if a heat-sensitive object such as an acrylic sheet or the like is located near the nozzle (focal point), such an object may melt due to the heat. Especially in cleaning an oral cavity, the use of such a nozzle may cause a low-temperature burn of the gums or the like. Therefore, the use of such a water-flow ultrasonic cleaning device is not considered in the field of dental treatment.

The ultrasonic foreign-body removal device as shown in Patent Document 1 employs ultrasonic waves that are comparatively low in frequency (30 kHz to 50 kHz). In using such low-frequency ultrasonic waves in such a water-flow ultrasonic cleaning device, the direction of said waves will be sharp, with the focal point of the waves defocused, thus making it impossible to obtain sufficient acoustic pressure to remove plaque or the like. Also, in using such low-frequency ultrasonic waves, the diameter of the ultrasonic transducer may become bigger to converge the ultrasonic waves to a certain extent, in which case the size of such a cleaning device may be larger, thus making it difficult to be used practically as an ultrasonic cleaning device for dental treatment.

This invention was achieved in light of the foregoing circumstances to provide a water-flow ultrasonic cleaning device and water-flow ultrasonic oral-cavity cleaning device and method of water-flow ultrasonic oral-cavity cleaning for surely and efficiently cleaning oral cavities.

Means for Solving the Problems

To solve the aforementioned problems, the first aspect of this invention refers to a water-flow ultrasonic oral-cavity cleaning device to clean oral cavities ultrasonically by a water-flow of cleaning liquid in which ultrasonic waves are propagated, characterized by a case comprising an ultrasonic transducer to propagate the ultrasonic waves into the cleaning liquid, a transducer mounting part provided at one end of the case to mount the ultrasonic transducer, a supply port to supply the cleaning liquid to a vibrating surface of the ultrasonic transducer, an outlet port provided on the apical end that is tapered toward the other end against the transducer mounting part to emit water flow of the cleaning liquid, by a cleaning-liquid supplying means that is connected to the supply port to supply the cleaning liquid into the case, and by a cleaning-liquid discharging means to discharge the cleaning liquid which was used in ultrasonically oral-cavity cleaning, whereof the oscillation frequency to activate the ultrasonic transducer is 100 kHz or more and 3 MHz or less, and the diameter of the ultrasonic transducer is 50 mm or less, and the power supply to the ultrasonic transducer is 100 W or less.

The first aspect of this invention allows for the cleaning liquid of the cleaning-liquid supplying means to be supplied into the case, and for the ultrasonic transducer that is mounted on the transducer mounting part within the case to propagate the ultrasonic waves into the cleaning liquid. The apical end of the case is tapered toward the outlet port, and the flow of the cleaning liquid propagated by the ultrasonic waves within the case is converged at the apical part and emitted from the outlet port into the oral cavity. The oscillation frequency (ultrasonic wave frequency) of the ultrasonic transducer used in this invention is 100 kHz or more and 3 MHz or less, and the diameter of the ultrasonic transducer is 50 mm or less, in which case the ultrasonic waves are moderately converged according to (the size of) the width of the treatment portion near the outlet port. The electric supply to the ultrasonic transducer is 100 W or less, thus avoiding problems such as low-temperature burning of the gums or the like caused by the ultrasonic waves being too high of acoustic pressure. As such, applying the flow of water into the oral cavity surely activates ultrasonic waves of moderate acoustic pressure, thus efficiently removing plaque, microorganisms on the oral mucosa, food residue or the like. After ultrasonically cleaning an oral cavity, the used cleaning liquid is discharged through the cleaning-liquid discharging means. Of the water-flow ultrasonic oral-cavity cleaning device of this invention, the diameter of the ultrasonic transducer is 50 mm or less, thus making said device compact, thus enabling a user to hold and easily handle the case, thus allowing him to clean an oral cavity efficiently and completely.

The second aspect of this invention refers to a water-flow ultrasonic oral-cavity cleaning device to clean an oral cavity ultrasonically by a water-flow of cleaning liquid in which ultrasonic waves are propagated, characterized by a case comprising an ultrasonic transducer to propagate the ultrasonic waves into the cleaning liquid, a transducer mounting part provided at one end of the case to mount the ultrasonic transducer, a supply port to supply the cleaning liquid to a vibrating surface of the ultrasonic transducer, and an outlet port provided on the apical end that is tapered toward the other end against the transducer mounting part to emit water flow of the cleaning liquid, by a cleaning-liquid supplying means that is connected to the supply port to supply the cleaning liquid into the case, and by a cleaning-liquid discharging means to discharge the cleaning liquid which was used in ultrasonically oral-cavity cleaning, whereof the value calculated by the arithmetic expression f×D×P is 500 or less under the condition that the oscillation frequency to activate the ultrasonic transducer is 100 kHz or more, the frequency is f (kHz), the diameter of the ultrasonic transducer is D(m), and the average power supply to the ultrasonic transducer is P (W).

The second aspect of this invention, like the first aspect, allows for the activation of ultrasonic waves of appropriate acoustic pressure to treat the oral cavity and efficiently to remove plaque, microorganisms on the oral mucosa, and food residue or the like. Also, the size of the ultrasonic transducer is compact, thus enabling the user to hold and easily handle the case, thus allowing him to clean the oral cavity efficiently and completely regardless of his technique.

The third aspect of this invention refers to the cleaning device according to the first or second aspect of this invention, wherein a bendable nozzle is provided at the outlet port of the case, thus allowing for a change in direction of the water-flow, and the bendable nozzle is bent at an angle of 5 degrees or more to 90 degrees or less with respect to the central axis.

According to the third aspect of this invention, the bendable nozzle provided at the outlet port of the case makes it possible to change the direction of the water-flow from an angle of 5 degrees or more to 90 degrees or less with respect to the central axis within the case, thus making it possible to apply the water-flow completely onto the back side of the front teeth, onto the back molars, and onto the interdentium or the like.

The fourth aspect of this invention refers to the cleaning device according to the third aspect of this invention, wherein the bendable nozzle is bent once in the opposite direction to an aperture of the nozzle-end and then bent again toward the nozzle-end, with a reflector being provided in the bent portion of the bendable nozzle to reflect the ultrasonic waves in the direction of the aperture.

According to the fourth aspect of this invention, bending the bendable nozzle allows for the direction of the water-flow to be changed from an angle of 5 degrees or more to 90 degrees or less with respect to the central axis within the case. As such, the water-flow can surely be applied to the backside of the front teeth, to the back molars, and to the interdentium or the like. Also, the reflector provided within the bent portion can surely reflect the ultrasonic waves to the nozzle end, thus making it possible to transmit the ultrasonic waves completely to the back side of the front teeth, to the back molars, and to the interdentium or the like.

The fifth aspect of this invention refers to the cleaning device according to the fourth aspect of this invention, wherein the end of the bendable nozzle is set on the central axis of the case.

According to the fifth aspect of this invention, the nozzle end is placed on the central axis of the case, thus making it easy to place the nozzle end at the position corresponding to the portion in the oral cavity being treated, so as to clean the oral cavity surely and efficiently.

The sixth aspect of this invention refers to the cleaning device according to any one of the third to fifth aspects, wherein an aperture diameter of the bendable nozzle is greater than a wavelength of the ultrasonic waves.

According to the sixth aspect of this invention, the diameter (of the nozzle) aperture end is greater than that of the ultrasonic waves, thus reducing the reflection of the ultrasonic waves at the nozzle end. Therefore, such ultrasonic waves are not decayed and are propagated to the water-flow, thus making it possible to activate the ultrasonic waves surely onto the portion of the oral cavity being treated.

The seventh aspect of this invention refers to the cleaning device according to any one of the first to sixth aspects of this invention, wherein the cleaning-liquid discharging means comprises an intake port shaped like a fan.

According to the seventh aspect of this invention, the intake-suction part of the cleaning-liquid discharging means is shaped like a fan, thus surely making it possible to suck and discharge the used cleaning liquid being dropped onto the portion of the oral cavity being treated.

The eighth aspect of his invention refers to the cleaning device according to any one of the first to seventh aspects of this invention, wherein a light-emitting means is provided inside the case to emit light to the water-flow.

According to the eighth aspect of this invention, the light propagate into the water-flow through the light-emitting means is emitted from the outlet port together with the water-flow. As such, the water-flow cleaning point can be indicated by the light, thus making it possible surely to clean the oral cavity.

The ninth aspect of this invention refers to the cleaning device according to any one of the first to seventh aspects of this invention, wherein a light-emitting means is provided on at least two external-wall portion that is tapered toward the outlet port so that a cleaning point is indicated where beams of light emitted from each light-emitting means Cross.

According to the ninth aspect of this invention, the ultrasonic acoustic-pressure being emitted from the ultrasonic transducer changes, according to the distance from said transducer, and the cleaning point of appropriate acoustic-pressure to clean the oral cavity is indicated where the beams of light cross. Thus, by applying the cleaning point indicated by the crossing point to the treatment portion, it is surely and efficiently possible to clean the oral cavity.

The 10th aspect of this invention refers to the cleaning device according to the eighth or ninth aspect of this invention, wherein at least one of the light-emitting means emits light of a wavelength of 465 nm.

According to the 10th aspect of this invention, light of a wavelength of 465 nm is emitted from the light-emitting means into the oral cavity. When light of 465 nm wavelength is emitted onto the teeth of an oral cavity, the plaque containing gram-negative bacteria causing periodontal disease is found by the red-reflected light that shows the level of plaque to be removed.

The 11th aspect of this invention refers to the cleaning device according to any one of the first to 10th aspects of this invention, wherein a bubbling means to bubble carbon-dioxide gas into the cleaning liquid of the cleaning-liquid supplying means is provided.

According to the 11th aspect of this invention, the air contained in the cleaning liquid is displaced by the carbon-dioxide gas, thus suppressing the sonochemical reaction by ultrasonic insonification.

The 12th aspect of this invention refers to the cleaning device according to any one of the first to 11th aspects of this invention, wherein the cleaning-liquid discharging means comprises a joint which can be connected to a vacuum device or to an electric-pump suction tube provided on a dental-treatment unit or to an aspiration tube provided on a hospital bed.

According to the 12th aspect of this invention, the existing equipment of a dental-treatment unit or in a hospital can be used, so that after cleaning an oral cavity, the cleaning liquid can be discharged, thus reducing equipment cost.

The 13th aspect of this invention refers to a method of a water-flow ultrasonic oral-cavity cleaning for cleaning an oral cavity ultrasonically by a water-flow of cleaning liquid in which ultrasonic waves are propagated, wherein the method comprises a step of propagating ultrasonic waves of a frequency of 100 kHz or more or 3 MHz or less into the cleaning liquid by supplying electric power of 100 W or less to an ultrasonic transducer of a diameter of 50 mm or less, and another step of emitting the water-flow of the cleaning liquid in which the ultrasonic waves are propagated into an oral cavity so that the treatment portion is treated with the ultrasonic waves by applying the water-flow thereon.

According to the 13th aspect of this invention, the ultrasonic waves being emitted from the ultrasonic transducer are moderately converged according to the width of the treatment portion near the outlet port, thus efficiently removing the plaque, microorganisms on the oral mucosa, food residue or the like. As such, the user can efficiently and completely clean the oral cavity regardless of his technique.

The 14th aspect of this invention refers to a method of a water-flow ultrasonic oral-cavity cleaning for cleaning an oral cavity ultrasonically by a water-flow of cleaning liquid in which ultrasonic waves are propagated, wherein the method comprises a step of propagating ultrasonic waves into the cleaning liquid using an ultrasonic transducer, whereof the value calculated by the arithmetic expression $f \times D \times P$ is 500 or less under the condition that the oscillation frequency to activate the ultrasonic transducer is 100 kHz or more, the frequency is $f$ (kHz), the diameter of the ultrasonic transducer is $D$(m), and the average power supply to the ultrasonic transducer is $P$ (W), and another step of emitting the water-flow of the cleaning liquid in which the ultrasonic waves are propagated into the oral cavity so that the treatment portion is treated with the ultrasonic waves by applying the water-flow thereon.

According to the 14th aspect of this invention, it is possible to activate the ultrasonic waves by an acoustic pressure appropriate for treating the oral cavity by efficiently removing the plaque, microorganisms on the oral mucosa, food residue or the like. As such, the user can efficiently and completely clean the oral cavity regardless of his technique.

Effect of the Invention

As detailed above, the first to 14th aspects of this invention make it possible to clean the oral cavity efficiently and completely.

MODES FOR CARRYING OUT THE INVENTION

Hereinafter, the embodiments of the water-flow ultrasonic oral-cavity cleaning device of this invention are described in reference to the drawings.

Figure 1:
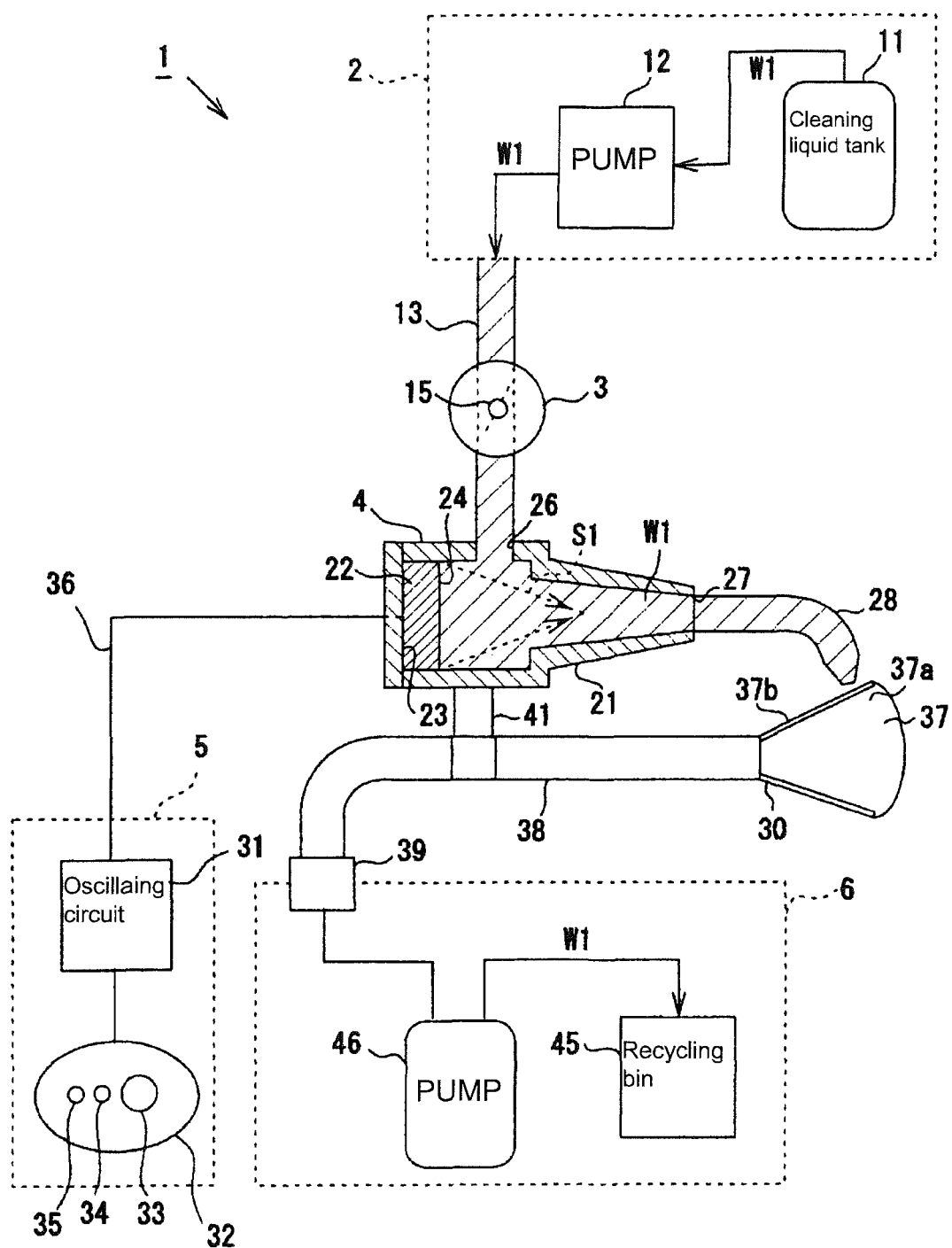
FIG. 1 is a skeleton framework showing the embodiment of the water-flow ultrasonic oral-cavity cleaning device.

FIG. 1 is a skeleton framework showing the embodiment of the water-flow ultrasonic oral-cavity cleaning device 1. As shown in FIG. 1, the water-flow ultrasonic oral-cavity cleaning device 1 comprises a cleaning-liquid supplying device 2 (cleaning-liquid supplying means), a water-flow controller 3, a cleaning-device unit 4, an ultrasonic-control device 5, and a water-suction discharging device 6. The water-flow ultrasonic oral-cavity cleaning device 1 allows for the cleaning of an oral cavity ultrasonically by a water-flow of cleaning liquid W1 propagated by ultrasonic waves S1.

The cleaning-liquid supplying device 2 comprises a cleaning-liquid tank 11 that holds the cleaning liquid W1, as well as a pump 12 that is connected to the cleaning-liquid tank 11. The cleaning-liquid supplying device 2 is connected to the cleaning-device unit 4 by the supply tube 13 through which the cleaning liquid W1 within the tank 11 is supplied to the cleaning-device unit 4 upon activating the pump 12.

A water-flow controller 3 is provided within the supply tube 13 connecting the cleaning-liquid supplying device 2 to the cleaning-device unit 4, thereon the water-flow controller 3 a flow-adjuster 15 is provided to adjust the water-flow of the cleaning liquid W1. The water-flow controller 3, according to the flow-adjuster 15 operational level, keeps the volume of cleaning liquid W1 being supplied to the cleaning-device unit 4 between 3 L to 0.1 L/min.

The cleaning-device unit 4 comprises a transducer case 21 shaped like a pen and an ultrasonic transducer 22 shaped like a disk, which is set within the transducer case 21 to propagate ultrasonic waves S1 of 400 kHz frequency into the cleaning liquid W1. The diameter of the ultrasonic transducer 22 is, for example, 30 mm. Regarding the transducer case 21, the ultrasonic transducer 22 is set against the transducer-affixed part 23 at the rear end, left side (as shown in FIG. 1), of the transducer case 21. A supply port 26, connected to the supply tube 13, is provided to supply the cleaning liquid W1 to the vibrating surface 24 of the ultrasonic transducer 22 at the rear of the transducer case 21 which is tapered toward the front end, right side (as shown in FIG. 1), and which is opposite the ultrasonic transducer 22 and incorporates an outlet port 27 through which pours the water-flow of the cleaning liquid W1.

Figure 3:
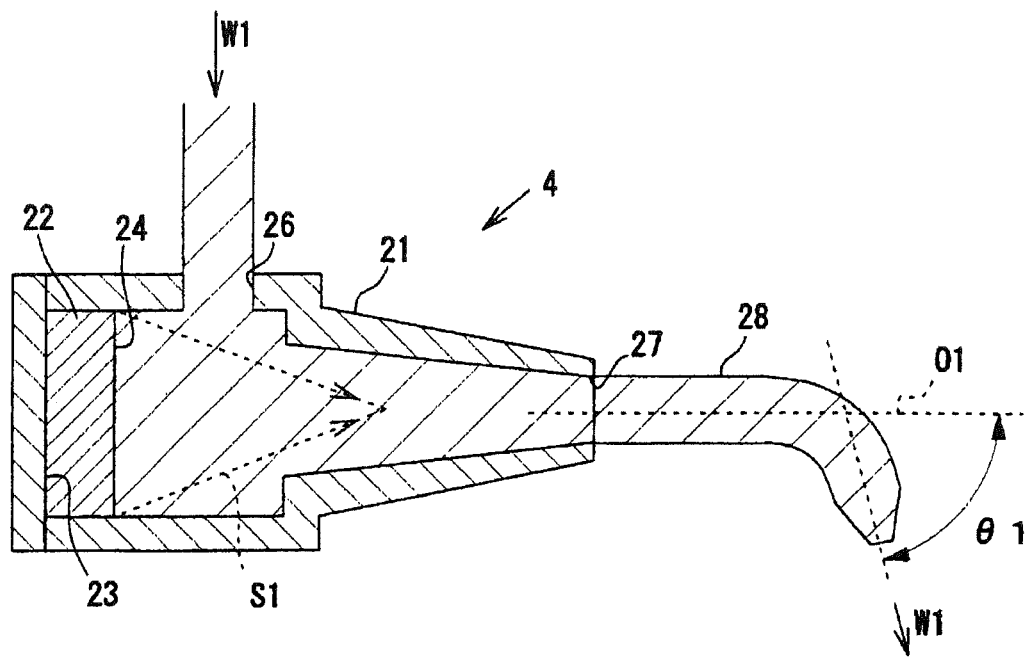
FIG. 3 is a cross-sectional view of the cleaning device.

Regarding the embodiment of this invention, the outer diameter of the transducer case 21 is of a handy size, being for example about 40 mm. The inner diameter of the rear end of the transducer case 21 is 30 mm, matching about the diameter of the ultrasonic transducer 22. The diameter of the outlet port 27 at the front end of the transducer case 21 is, for example, about 5 mm, and the distance between the vibrating surface 24 of the ultrasonic transducer 22 and the outlet port 27 is, for example, 50 mm. Regarding the cleaning-body unit 4 of the embodiment, a bendable nozzle 28 is provided on the outlet port 27 of the transducer case 21 to allow for changing the direction of the water-flow. The bendable nozzle 28 is bent such that the direction of the water-flow faces the side of the suction nozzle 30 (cleaning-liquid discharging means). Specifically, as shown in FIG. 3, the end of the nozzle 28 is bent at angle θ1 of 5 to 90 degrees with respect to the central axis O1 of the transducer case 21. The aperture-diameter (nozzle diameter) of the end of the bendable nozzle 28 is 4 mm and is greater than the diameter of the ultrasonic waves. Of this embodiment, the frequency of the ultrasonic waves is 400 kHz, and the acoustic speed of the cleaning liquid W1 is 1,500/s, so that the ultrasonic waves are 3.75 mm (=1,500 m÷400 kHz).

Of this embodiment, the cross-sectional shape of the outlet port 27 of the transducer case 21 and the nozzle 28 are circular. The angle θ1 of the bendable nozzle 28 can either be specified or freely adjustable. For example, the nozzle 28 can be formed of an accordion tube, with the angle θ1 of the nozzle 28 being adjustable. It is possible to rotate the nozzle 28 in any direction respective of the central axis O1 of the transducer case 21. It is also possible to change the length of the bendable nozzle 28 to reach any treatment-portion of the oral cavity being treated, whether the back molars, the front teeth, or the interdentium or the like. For example, for cleaning the front teeth, a nozzle of about 2 cm long is used, and for cleaning the back molars, a nozzle about 5 cm long is used.

Of this embodiment, the transducer case 21 and bendable nozzle 28 are made of a metal such as stainless steel or the like, or they can be made of glass, ceramic, or resin or the like.

As shown in FIG. 1, the ultrasonic control device 5 comprises an oscillating circuit 31 and a foot switch 32 that is operated by the user's foot and comprises an output switch 33 for switching ON or OFF the ultrasonic waves S1 and selector switches 34, 35 for changing the ultrasonic-output mode (to either continuous or burst) or the like.

The foot switch 32 engages the oscillating circuit 31 according to the operational status of switches 33 to 35. The oscillating circuit 31 is connected electrically to the ultrasonic transducer 22 of the cleaning-device unit 4 by the wire 36 and transmits the driving-signal to the ultrasonic transducer 22 according to the signal from the foot switch 32. In selecting continuous mode for emitting the ultrasonic waves S1, the ultrasonic transducer 22 vibrates continuously. In selecting burst mode, the ultrasonic transducer 22 vibrates intermittently. Of this embodiment, the average amount of electricity supplied to the ultrasonic transducer 22 from the oscillating circuit 31 of the control device 5 is approximately 12 W. The oscillation frequency of the oscillating circuit 31 is 400 kHz.

Figure 2:
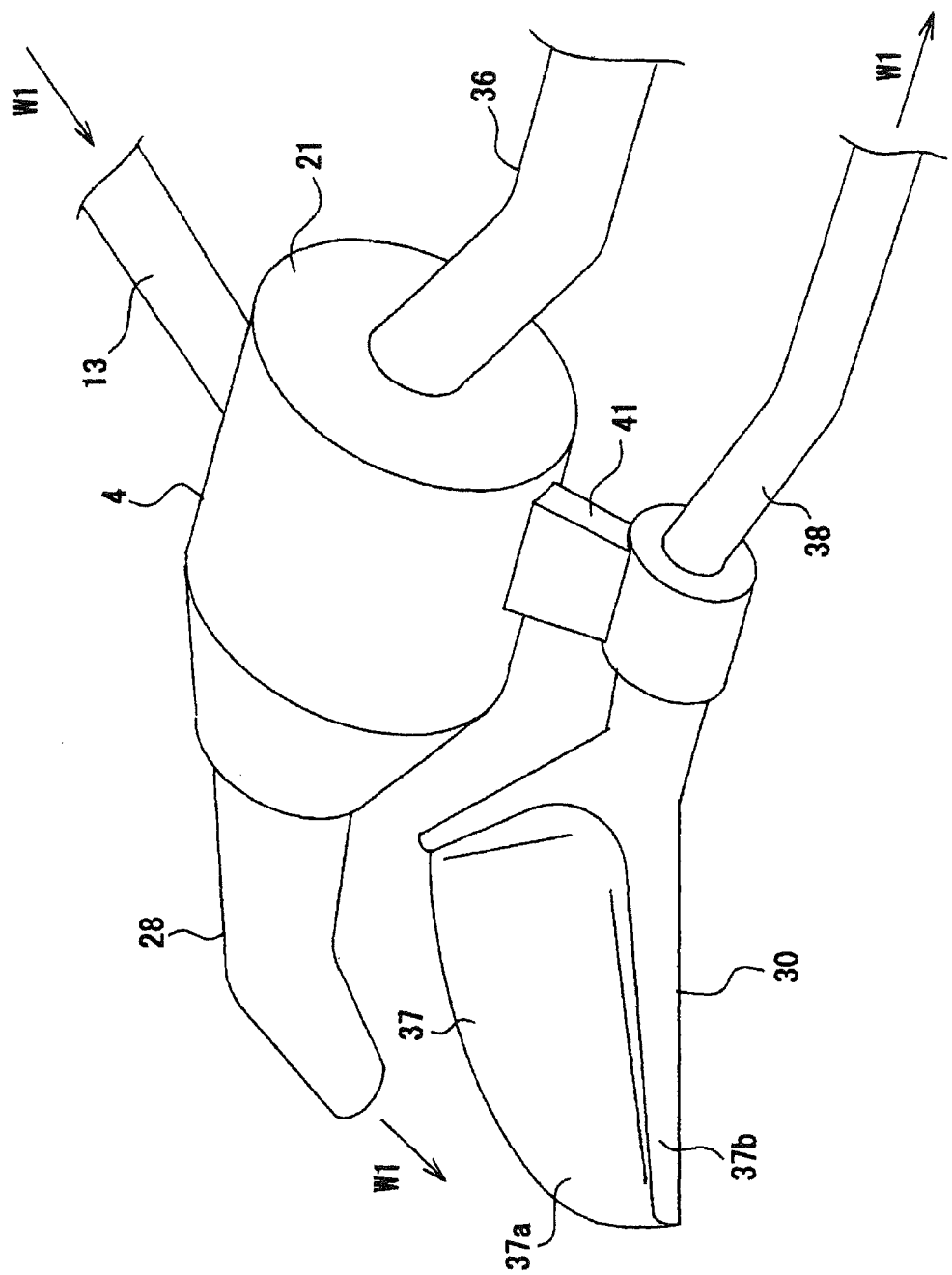
FIG. 2 is an oblique perspective-view showing the unit of the cleaning device and suction nozzle.
Figure 4:
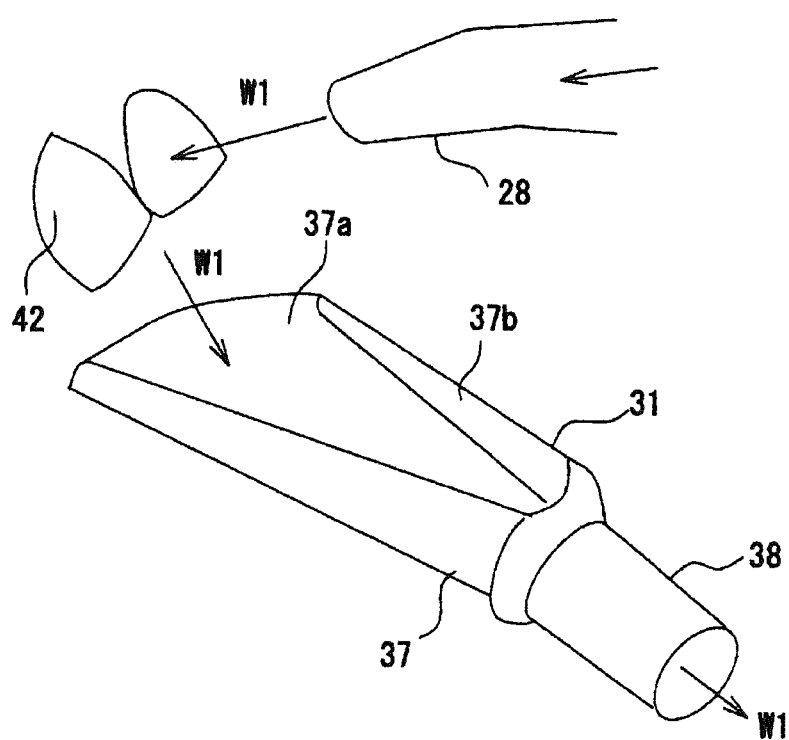
FIG. 4 is an explanatory diagram showing the cleaning method of the water-flow ultrasonic oral-cavity cleaning device.

The suction nozzle 30 comprises a spreading suction port 37 shaped like a fan like a ginkgo leaf. A suction tube 38 connects the suction port 37 to the joint 39 provided at the base end of the suction tube 38, and the joint 39 is connected to the water-suction discharge device 6. As shown in FIG. 2, the suction nozzle 30 of the embodiment is affixed to a gripper 41 protruding from the transducer case 21. The suction port 37 of the suction nozzle 30 comprises a fan-shaped bottom portion 37a and a guide portion 37b, and the guide portion 37b is formed on both sides of the bottom portion 37a to receive the used cleaning liquid W1 from the base of the treatment portion (e.g. the teeth) and to discharge said liquid W1 after ultrasonically cleaning the oral cavity (see FIG. 4). The treatment portion 42 includes a dental implant besides the surface or root of a tooth.

As shown in FIG. 1, the water-suction discharging device 6 comprises a container 45, in which the cleaning liquid W1 is collected, and a pump 46. In activating the pump 46 of said device 6, the cleaning liquid W1 is sucked by the suction nozzle 30 and collected into the recycling bin 45.

Of this embodiment, household electricity (not shown in drawings) is used to power the water-flow ultrasonic oral-cavity cleaning device 1. Alternatively, an electric battery can be used to power the said device 1, so that it can be used at any place where household electricity is unavailable.

Hereinafter, the method for cleaning an oral cavity by using the water-flow ultrasonic oral-cavity cleaning device 1 is described.

The user (dentist) holds the cleaning-device unit 4 with one hand and places the apical-end of the bendable nozzle 28 onto the treatment portion 42 of the patient whilst placing the fan-shaped suction port 37 of the suction nozzle 30 onto the downside of the treatment portion 42. In other words, the treatment portion 42 is clipped between the bendable nozzle 28 and the suction nozzle 30 (see FIG. 4). The user also operates the modes 34, 35 of the foot switch 32 to select the output mode of the ultrasonic waves S1. He also operates the flow-adjuster 15 of the water-flow controller 3 to set the water-flow of the cleaning liquid W1, for example, at 0.9 L/min. Then, he engages the power switch (not shown in the drawing) of the cleaning-liquid supplying device 2 and the water-suction discharging device 6 to activate pumps 12 and 46 whilst engaging the output switch 33 of the foot switch 32 to activate the oscillating circuit 31.

Thus, the cleaning liquid W1 is now being supplied to the cleaning-device unit 4 from the cleaning-liquid supplying device 2, and the ultrasonic waves S1 of 400 kHz are being propagated into the cleaning liquid W1 from the ultrasonic transducer 22 within the transducer case 21 of the cleaning-device unit 4. The apical-end of the transducer case 21 is tapered toward the outlet port 27, and the water-flow of the cleaning liquid W1, which is being propagated by the ultrasonic waves S1, is converging at the apical-end of the transducer 22 and being applied to the treatment portion 42 in the oral cavity by the outlet port 27 and the bendable nozzle 28, thus functioning the ultrasonic waves S1 being propagated into the cleaning liquid W1 to the treatment portion 42, thus removing the dirt of the treatment portion 42 (such as viscous plaque, microorganisms on the oral mucosa, food residue or the like). The user then vacuums the cleaning liquid W1 after cleaning by the suction nozzle 30 and discharges (collects) the used cleaning liquid into the recycling bin 45 of the water-suction discharging device 6.

As such, after ultrasonically cleaning the oral cavity of the patient, the user turns off the output switch 33 of the foot switch 32, the power switch (not shown in drawing) or the like, to stop the devices 2, 5 and 6, thus completing the ultrasonic cleaning.

Figure 5:
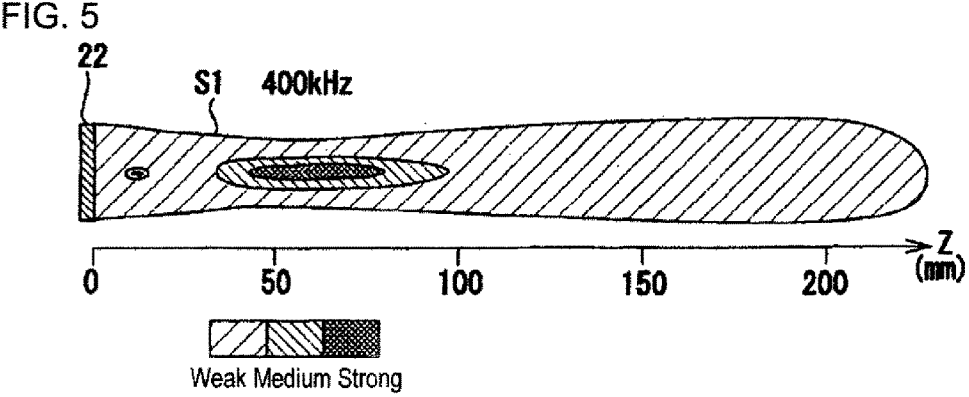
FIG. 5 is an explanatory diagram showing the distribution of 400 kHz of ultrasonic acoustic pressure.
Figure 6:
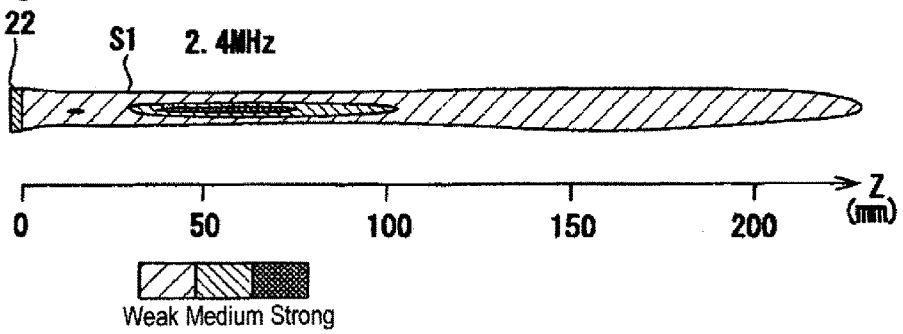
FIG. 6 is an explanatory diagram showing the distribution of 2.4 MHz of ultrasonic acoustic pressure.

The inventors by simulation verified the acoustic pressure of 400 kHz ultrasonic waves S1 being emitted from the ultrasonic transducer 22. The result is shown in FIG. 5. FIG. 6 shows the simulation result in the case of 2.4 MHz ultrasonic waves S1 are emitted, whilst FIG. 7 shows the simulation result in the case of 200 kHz ultrasonic waves S1 are emitted.

As shown in FIG. 5, this embodiment shows a high acoustic-pressure zone when the distance from the ultrasonic transducer 22 is 40 mm (in the vicinity of the outlet port 27 of the transducer case 21) to 100 mm (in the vicinity of the apical-end of the nozzle 28). Compared to the case of high frequency (2.4 MHz), as shown in FIG. 6, it was revealed that the acoustic pressure-zone spreads gently radially throughout the ultrasonic transducer 22, and there is no strong convergence. This embodiment uses an ultrasonic transducer 22 of 30 mm in diameter. However, the actual area that prorogates the ultrasonic waves S1 was 26 mm in diameter. Also, in case of 2.4 kHz, as shown in FIG. 6, an ultrasonic transducer 22 with an actual diameter of 30 mm is used to obtain the focal point of the ultrasonic waves S1 in the vicinity of 50 mm.

Figure 7:
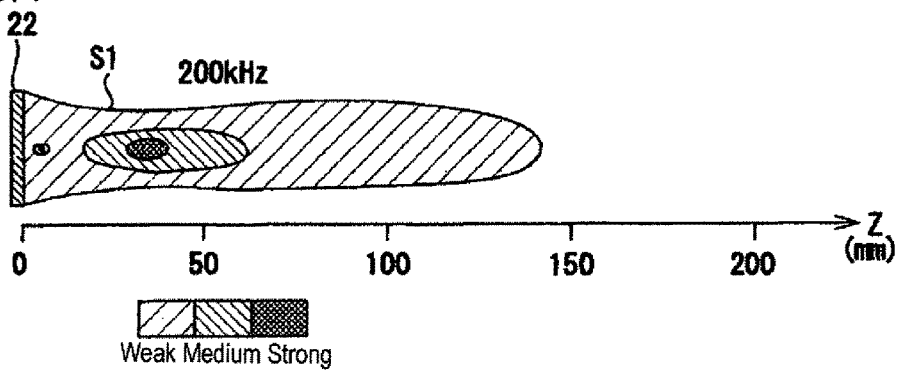
FIG. 7 is an explanatory diagram showing the distribution of 200 kHz of ultrasonic acoustic pressure.

As shown in FIGS. 5 to 7, the convergence is strong in a range of higher frequency and is moderate in a range of lower frequency. However, the lower the frequency, the shorter the convergence zone (in a z-axis direction that is the axial direction of the transducer 22) where the ultrasonic waves S1 converge and the acoustic pressure becomes higher. When widening the convergence zone in the z-direction, it is necessary to enlarge the diameter of the ultrasonic transducer 22. Based on these simulation results, it is necessary to consider the following three points: the cleaning should be done efficiently without too much convergence of the ultrasonic waves S1; the diameter of the ultrasonic transducer 22 should be small; and that the oscillation frequency (frequency of the ultrasonic waves S1) of the ultrasonic transducer 22 should be 100 kHz or more to 3 MHz or less, thus making it possible to efficiently clean the oral cavity.

Especially, whilst surely cleaning the micro-dirt from the teeth, it is preferable to use the high-frequency ultrasonic waves S1, in which case the average power supply to the ultrasonic transducer 22 should be lowered. Accordingly, the level of frequency and the diameter of the transducer should be smaller. More specifically, the value calculated by the arithmetic expression f×D×P is 500 or less, under the condition that the oscillation frequency to activate the ultrasonic transducer is 100 kHz or more and the frequency of the ultrasonic transducer 22 is f (kHz), and that the diameter of the ultrasonic transducer is D (m), and the average power supply to the ultrasonic transducer is P (W).

As a reference, the water-flow ultrasonic cleaner for semiconductors can clean the following conventional products A, B and C. Product A is a cleaner of which the frequency f is 400 kHz, the diameter D of the transducer is 0.04 m, and the power supply P is 100 W. Product B is a cleaner of which the frequency f is 1 MHz, the diameter D of the transducer is 0.020 m, and the power supply P is 60 W. Product C is a cleaner of which the frequency f is 3 MHz, the diameter D of the transducer is 0.015 m, and the power supply P is 40 W.

Among products A to C, the value calculated by the arithmetic-expression frequency f (kHz)×transducer's diameter D (m)×power supply P (W) is 1,600 for product A, 1,200 for product B and 1,800 for product C, which are all beyond 500. Contrarily, if the value is set to be 500 or less by making the transducer's diameter D and the average power supply P smaller according to the frequency f, it is possible to activate the ultrasonic waves S1 with the appropriate acoustic pressure sufficient to clean the treatment portion 42 in the oral cavity, thus efficiently removing the plaque, microorganisms on the oral mucosa, food residue or the like.

Figure 8:
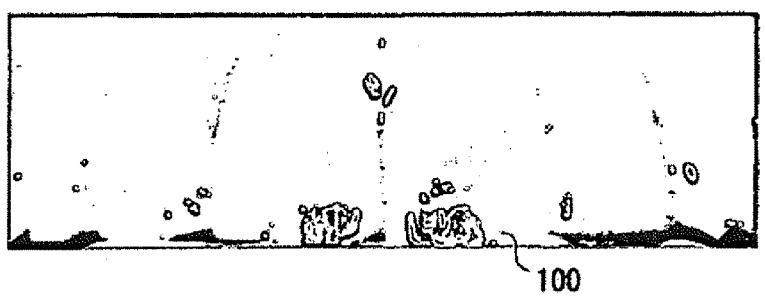
FIG. 8 is an explanatory diagram showing a photograph of the labial front teeth of the upper jaw prior to the ultrasonic oral-cavity cleaning.
Figure 9:
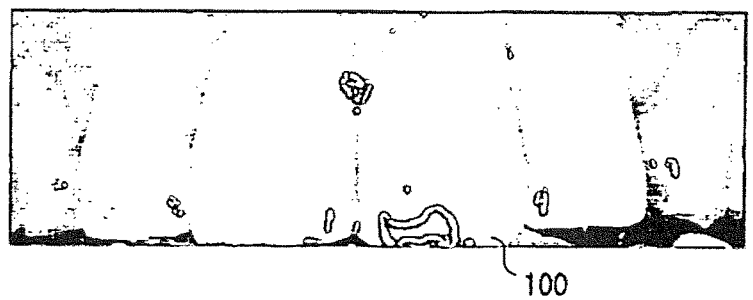
FIG. 9 is an explanatory diagram showing a photograph of the labial from teeth of the upper jaw after the ultrasonic oral-cavity cleaning.

The inventors verified the cleaning effect in removing the plaque attached on the labial front teeth of the upper jaw by using the water-flow ultrasonic oral-cavity cleaning device 1 of this invention. First of all, the inventors colored the plaque attached on the labial front teeth 100 of the upper jaw with the plaque disclosing solution (see FIG. 8). In a convenient manner, FIG. 8 shows a monochrome of the plaque attached on the front teeth 100 of the upper jaw. However, the actual color photo shows the portion of the plaque colored in red. The distance between the apical-point of the nozzle 28 of the cleaning device 1 and the surface of the tooth is kept to approximately 20 mm to activate the water-flow of the cleaning liquid W1 being propagated by the ultrasonic waves S1 from the bendable nozzle 28 to the plaque attached-portion for 60 seconds. The result is shown in FIG. 9. It was confirmed that the plaque colored in red on the front teeth 100 of the upper jaw had been removed after the cleaning.

Figure 10:
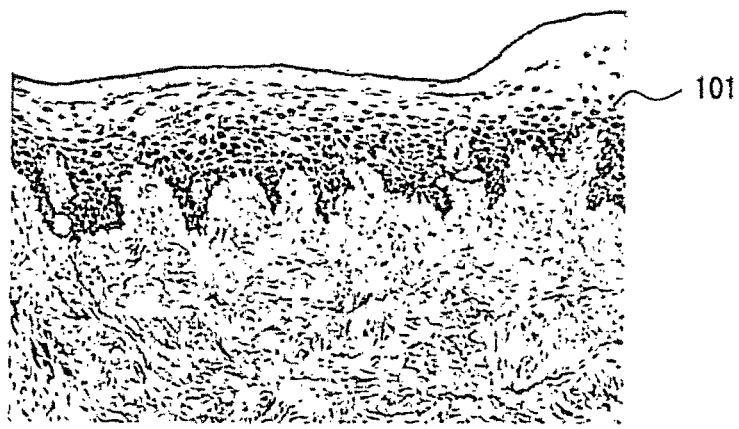
FIG. 10 is a cross-sectional view showing a histological image of the gingival mucosa of a miniature pig.

The inventors also tested the toutlet port-damage by using the water-flow ultrasonic oral-cavity cleaning device 1 in the following method. Specifically, the inventors cleaned the gingival mucosa of a miniature pig by using the bendable nozzle 28 such that the apical-end of the nozzle 28 was set approximately 20 mm away from the gingival mucosa and then by activating the water-flow of the cleaning liquid W1 being propagated by the ultrasonic waves S1 from the bendable nozzle 28 to the gingival mucosa for three minutes. FIG. 10 shows the outlet port image 101 after 24 hours of the cleaning procedure. As shown in FIG. 10, the neutrophils infiltration into the epidermis, or the mononuclear-cell infiltration into the lamina propria, was not observed. An acute inflammatory reaction like hydrops or the like was not observed, either. Therefore, it was concluded that the water-flow ultrasonic oral-cavity cleaning device 1 had no detrimental effect on the gingival outlet ports.

The inventors also revealed the cleaning effect on the dental implant (titanium mirror-like finish and surface roughening) by the water-flow ultrasonic oral-cavity cleaning device 1. Specifically, first of all, the inventors prepared the test pieces (mirror-like finish and surface roughened pieces) that have the same surface as the dental implant. Then, they affixed the pieces onto a removable denture base and kept it in the mouth of the patient for three days, so that plaque (biological film) formed on the surface of the teeth. After that, they removed the denture base from the mouth of the patient and clean it for three minutes by the water-flow ultrasonic oral-cavity cleaning device 1 under the condition that the power supply to the ultrasonic transducer 22 was 12 W, and the amount of water-flow was 0.3/min. Also, the plaque on the surface of the test piece was colored by the plaque-disclosing solution, and the state of the plaque was monitored before and after the cleaning by a digital microscope, thus calculating the plaque-removal ratio.

Figure 11:
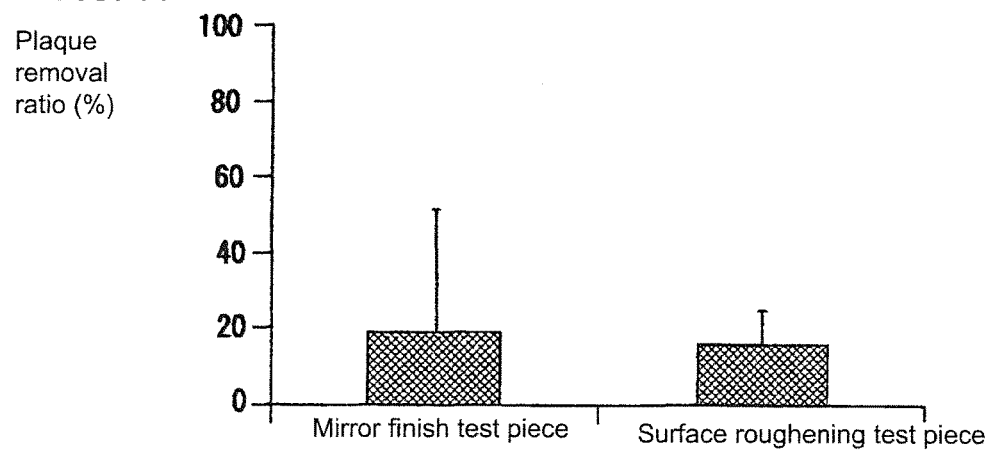
FIG. 11 is a graph showing the plaque-removal ratio by the ultrasonic oral-cavity cleaning.

Therein, the degradation and removal of the plaque attached to the surface of the test piece was three dimensionally measured by using an omnifocal-image (not shown in drawing). As a result, the plaque having a thickness of about 10 μm came off the surface of the test piece, and the metal surface was exposed. Also, the removal-ratio of the plaque was 80% or more for both the mirror-like finish and surface-roughened pieces (see FIG. 11).

Figure 12:
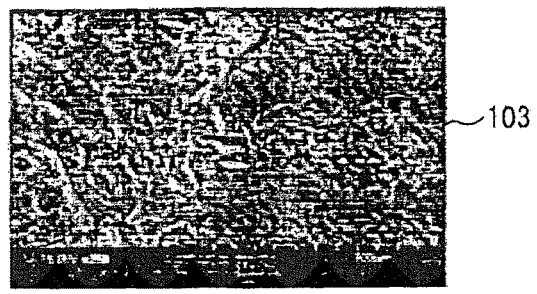
FIG. 12 is an explanatory diagram showing an SEM image of a test piece before the plaque was attached.
Figure 13:
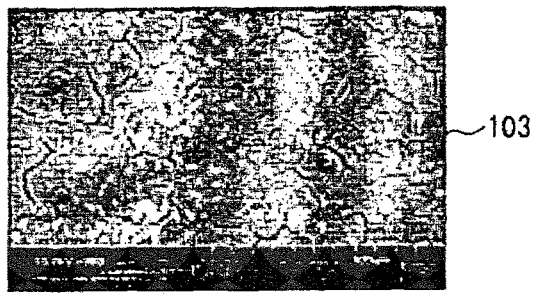
FIG. 13 is an explanatory diagram showing an SEM image of a test piece after the plaque was attached.
Figure 14:
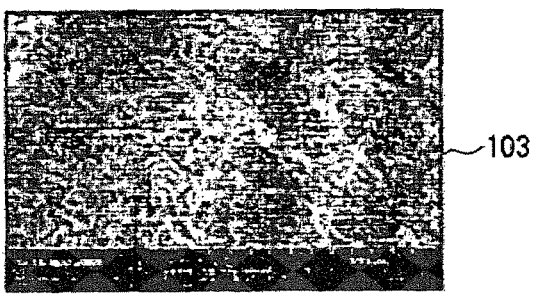
FIG. 14 is an explanatory diagram showing an SEM image of a test piece after the ultrasonic oral-cavity cleaning.

Also, the removal-level of bacteria was examined by a scanning electron microscope (SEM). Therein, the test-piece as an implant test-piece was used for the surface roughening, as shown in the SEM image of FIG. 12. As shown in FIG. 12, on the non-plaque contaminated surface, the concave-convex shape of the rough surface was observed. On the other hand, as shown in FIG. 13, it was observed that the plaque-attached surface of the test piece 103 was entirely filled with the bacterial mass and biological film. The water-flow cleaning (ultrasonic-wave injection) was made to the plaque-attached test piece 103 by using the water-flow ultrasonic oral-cavity cleaning device 1. As a result, as shown in FIG. 14, bacterial mass or biological film was not found on the surface of the test piece 103, and the concave-convex shape was found on the rough surface of the test piece 103. As such, the water-flow ultrasonic oral-cavity cleaning device 1 was found to be effective in removing the plaque from the dental implant when cleaning the oral cavity.

Therefore, the embodiment of this invention realizes the following effects.

(1) Of the water-flow ultrasonic oral-cavity cleaning device 1 of this invention, the oscillation frequency f of the ultrasonic transducer 22 is 400 kHz, and the diameter D of the transducer 22 is 30 mm. As such, the ultrasonic waves S1 are moderately converged according to the width (size of) the treatment portion 42 near the outlet port 27 of the transducer case 21. The electric supply P to the ultrasonic transducer 22 is 12 W, which is less compared to that of the conventional product, thus avoiding problems such as low-temperature burning of the gums or the like caused by the ultrasonic waves S1 being too high of an acoustic-pressure. Applying the water-flow into the treatment portion 42 of the oral cavity surely activates the ultrasonic waves S1 of a moderate acoustic-pressure, thus efficiently removing plaque, microorganisms on the oral mucosa, food residue or the like, thus allowing the user to clean an oral cavity efficiently and completely, regardless of his technique.

(2) Of the water-flow ultrasonic oral-cavity cleaning device 1 of this invention, it is preferable to configure the device 1 such that the value calculated by the arithmetic expression f×D×P is 500 or less under the condition that the oscillation frequency to activate the ultrasonic transducer is 100 kHz or more, and the frequency is f (kHz), and that the diameter of the ultrasonic transducer is D (m), and the average power supply to the ultrasonic transducer 22 is P (W). Especially, when the oscillation frequency f is 200 kHz to 500 kHz, it is preferable to configure the device 1 such that the value calculated is 200 or less. Specifically, for example, when the oscillation frequency f of the ultrasonic transducer 22 is 400 kHz, the diameter D of the transducer is 0.03, and the average power supply P is 12 W, and the value is 144. Thus, applying the water-flow into the treatment portion 42 of the oral cavity surely activates ultrasonic waves S1 of a moderate acoustic pressure, thus efficiently removing plaque, microorganisms on the oral mucosa, food residue or the like.

(3) Of the water-flow ultrasonic oral-cavity cleaning device 1 of this embodiment, the diameter D of the ultrasonic transducer 22 is 30 mm, thus making the cleaning-device unit 4 compact. Also, the cleaning-device unit 4 is pen-shaped, thus enabling a user to hold and handle the cleaning-device unit 4 with one hand. Specifically, the user can hold the device unit 4 with one hand and hold a mirror with the other hand, thus enabling him to check the position of the treatment portion 42 by the mirror and to clean the oral cavity completely.

(4) Of the water-flow ultrasonic oral-cavity cleaning device 1 of this embodiment, the bendable nozzle 28 provided at the outlet port 27 of the transducer case 21 makes it possible to change the direction of the water-flow from an angle θ1 of 5 degrees or more to 90 degrees or less with respect to the central axis O1 within the case 21, thus making it possible to apply the water-flow completely onto the back side of the front teeth, onto the back molars, and onto the interdentium or the like.

(5) Of the water-flow ultrasonic oral-cavity cleaning device 1 of this embodiment, the bendable nozzle 28 is such that the diameter of (the nozzle) aperture is greater than that of the ultrasonic waves S1. If the diameter of the aperture is smaller than that of the ultrasonic waves S1, the ultrasonic waves S1 will not exit the nozzle 28 due to the reflection, thus greatly decaying the ultrasonic waves S1 to be propagated into the water-flow. The reflection of the ultrasonic waves S1 means that they return to the ultrasonic transducer 22 from the apical-end of the nozzle. The greater the angle θ1 of the nozzle, the greater the reflection of the ultrasonic waves. Contrarily, the embodiment of this invention is formed such that the diameter of (the nozzle) aperture is greater than that of the ultrasonic waves S1, thus reducing the reflection of said waves S1 at the apical-end of the nozzle. Therefore, the ultrasonic waves are not decayed and will surely propagate into the water-flow. Eventually, the ultrasonic waves S1 are surely activated to the treatment portion 42 in the oral cavity.

(6) Of the water-flow ultrasonic oral-cavity cleaning device 1 of this embodiment, the suction nozzle 30 comprises an intake-suction part 37 shaped like a fan, thus surely making it possible to suck and discharge the used cleaning liquid being dropped onto the treatment portion 42 of the oral cavity (being treated).

(7) The water-flow ultrasonic oral-cavity cleaning device 1 of this embodiment comprises a water-flow controller 3 for adjusting the volume of the water-flow of the cleaning liquid W1, thus making it possible to adjust the water-flow appropriately to clean the treatment portion 42 (being treated). Also, regarding the ultrasonic-control device 5, the output-mode of the ultrasonic waves S1 can be switched either to continuous or burst by operating the foot-switch by foot, and the output of the ultrasonic waves S1 can also be controlled by the ON-OFF system. As such, the user can properly adjust the ultrasonic waves S1 to activate the treatment portion 42 (being treated), thus surely cleaning the oral cavity.

(8) The water-flow ultrasonic oral-cavity cleaning device 1 of this embodiment allows for controlling the volume of the water-flow of the cleaning liquid W1, thus making it much easier to use it at a clinical site. Also, plain water, instead of the cleaning liquid W1, can show the sufficient cleaning effect. In this case, it is unnecessary to use any medical agent such as detergent, which, ecologically speaking is excellent.

The embodiment of this invention can be modified, as follows.

Figure 15:
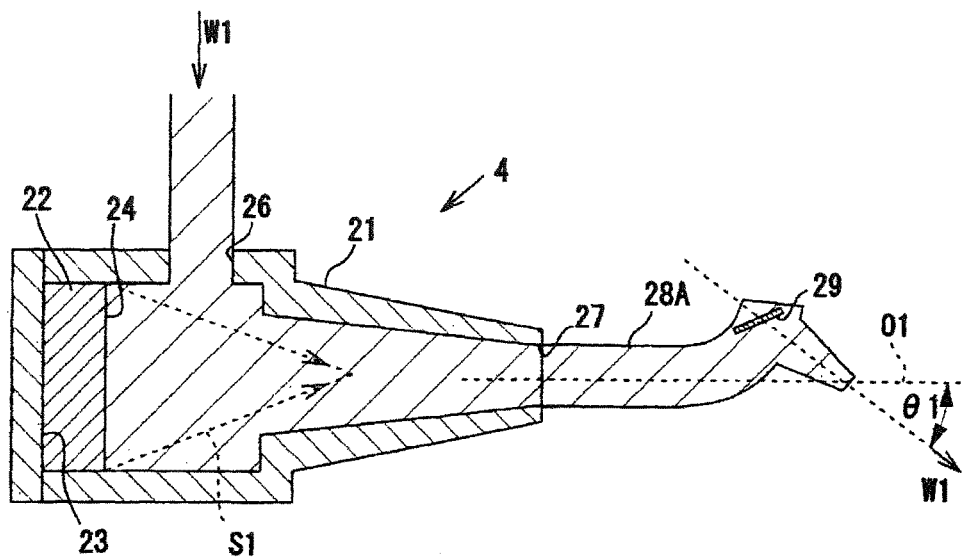
FIG. 15 is a cross-sectional view of the bendable nozzle used as another embodiment.

The above referenced embodiment of this invention comprises the bendable nozzle 28, which is provided on the outlet port 27 of the cleaning-device unit 4 and is bent downward (see FIG. 3). Yet, it is not limited to that direction. For example, such nozzle 28 includes the bendable nozzle 28A, as shown in FIG. 15, which is bent once in the opposite direction to the aperture of the nozzle-end and then bent again toward the nozzle-end. Also, regarding the bendable nozzle 28A, the angle θ1 at the apical-end of the nozzle is 5 degrees to 90 degrees with respect to the central axis O1 of the transducer case 21. Also, a reflector 29 is provided within the bent portion of the bendable nozzle 28A to reflect the ultrasonic waves 21 in the direction of the aperture. Moreover, the apical-end of the bendable nozzle 28A is placed on the central axis O1 of the transducer case 21. By using such a bendable nozzle 28A, the apical-end of the nozzle can be placed easily on the back side of the front teeth, on the back molars, and on the interdentium or the like, thus making it possible to apply the water-flow to them completely. Furthermore, the reflector is provided within the bent portion of the nozzle 28A, so that the ultrasonic waves 21 can surely be led to the apical-end of the nozzle, thus making it possible to surely activate the ultrasonic waves 21 to the back side of the front teeth, to the back molars, and to the interdentium or the like.

The above referenced embodiment of this invention comprises the bendable nozzles 28, 28A provided at the outlet port 27 of the cleaning device unit 4 to change the direction of the water flow. However, it is possible to configure the cleaning device unit 4 without the bendable nozzles 28, 28A so that the cleaning liquid W1 is directly outputted from the outlet port 27.

Figure 16:
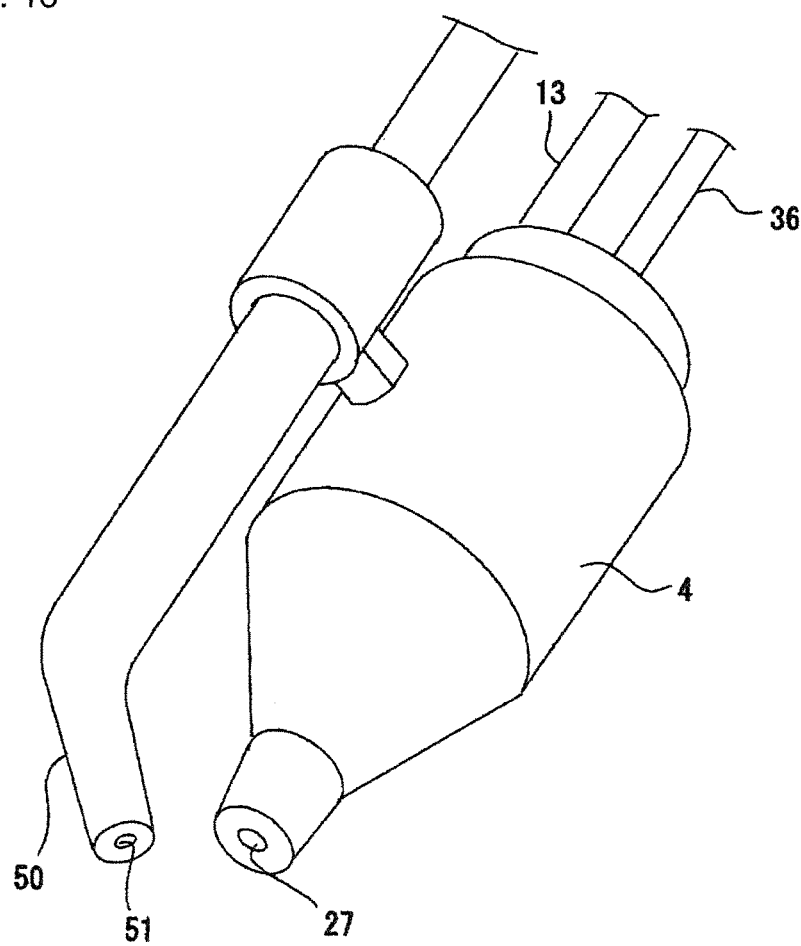
FIG. 16 is an oblique-perspective view of the cleaning device and the suction nozzle used as another embodiment.

The above referenced embodiment comprises a suction nozzle 30 as the cleaning-liquid discharging means, with the suction port 37 being shaped like a fan. However, it is not limited to being thus. For example, as shown in FIG. 16, a tube-shaped suction nozzle 50 can also be used. Of the suction nozzle 50, as shown in FIG. 16, a suction port 51 in the vicinity of the outlet port 27 of the cleaning-device unit 4 opens toward the cleaning point where the cleaning liquid W1 hits. The suction nozzle 50 allows for the rapid discharge of the used cleaning liquid W1 from the oral cavity during the ultrasonic cleaning.

Figure 17:
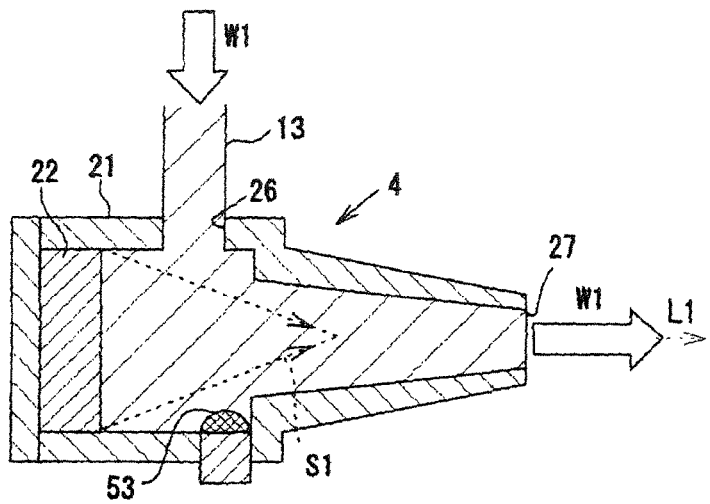
FIG. 17 is an oblique-perspective view of the cleaning device as another embodiment.
Figure 18:
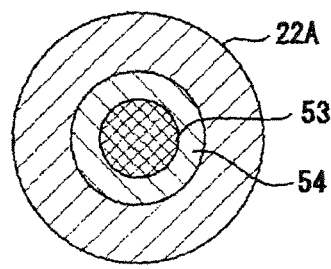
FIG. 18 is an oblique-perspective view of the cleaning device as another embodiment.
Figure 19:
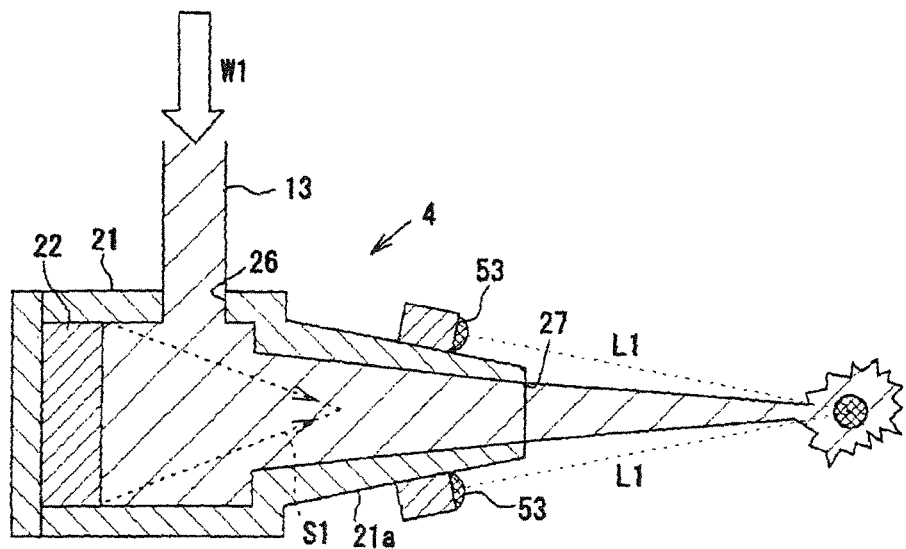
FIG. 19 is an oblique-perspective view of the cleaning device as another embodiment.

As shown in FIGS. 17, 18 and 19, it is possible to identify the cleaning point of the cleaning-device unit 4 by the light. Specifically, regarding the transducer case 21 of the cleaning-device unit 4 shown in FIG. 17, an LED 53 (a lighting means) is provided opposite the supply port 26 of the cleaning liquid W1 to emit the light L1 from LED 53 to the inside of the transducer case 21. In this case, the light L1 is propagated into the cleaning liquid W1 flowing within the transducer case 21, and the light L1 is emitted with the water-flow from the outlet port 27 provided at the apical-end of the case. The emitting direction of the light L1 indicates the cleaning point that the water-flow hits. Thus, it is possible to surely apply the water-flow to the treatment portion 42 necessary for the ultrasonic cleaning, thus making it possible to efficiently and rapidly clean the oral cavity.

Also, as shown in FIG. 18, it is possible to use an ultrasonic transducer 22A shaped like a ring (doughnut shape) and provide the LED 53 in the center thereof to emit the light L1 from LED 53 to the outlet port 27. Also, a vibration-damping material 54 such as rubber or the like is provided in the clearance between the LED 53 and the ultrasonic transducer 22A to prevent the light being emitted from the LED 53 from propagating to the ultrasonic waves S1. Such a transducer 22A having the LED 53 in the center, compared to the transducer as shown in FIG. 17 having the LED 53 at the side of the transducer case 21, emits a stronger light L1 to surely indicate the cleaning point.

As shown in FIG. 19, it is also possible to configure the transducer case 21 such that the LEDs 53 are provided on two places of the external wall 21a that is tapered toward the outlet port 27 to indicate the cleaning point where the beam of light L1 emitted from each LED 53 cross. In this case, the acoustic pressure of the ultrasonic waves S1 in the water-flow varies according to the distance from the ultrasonic transducer 22. However, it is possible to accurately indicate the appropriate cleaning point by the light L1 being emitted from the LED 53.

It is preferable to use a blue LED of a wavelength of 465 nm as the LED 53 emitting the light L1. In fact, it is said that plaque, especially plaque containing much gram-negative bacteria, is likely to cause periodontal disease, as such bacteria dissolves the red-blood cells and produces heme from hemoglobin. Such plaque has the characteristic of emitting weak red light against the light L1 of a wavelength of 465 nm. Therefore, if the user wears sunglasses to block the light L1 of 465 nm wavelength whilst cleaning the oral cavity, he can visually identify the removal-level of the plaque.

Figure 20:
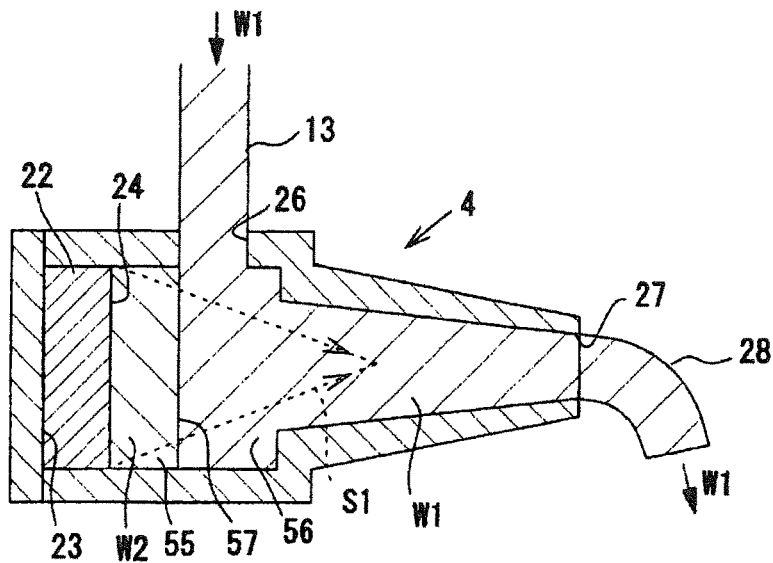
FIG. 20 is an oblique-perspective view of the cleaning device as another embodiment.

As shown in FIG. 20, it is also possible to configure the cleaning-device unit 4 such that the transducer case 21 incorporates a propagating-medium holding space 55 to hold an ultrasonic-propagating medium W2 (particularly water) on the vibrating surface 24 of the ultrasonic transducer 22, and a medium-holding material 57 to double the inner-space for the propagating-medium holding space 55, and a supplying space 56 for supplying the water-flow of the cleaning liquid W1. Regarding the medium-holding material 57 for separating the space into space 55 and 56, a thin film-material such as stainless-steel film, polyethylene film or the like is used. In this case, even if the cleaning liquid W1 is discharging from the supplying space 56 whilst cleaning is not being conducted, the ultrasonic-propagating medium W2 is surely held on the vibrating surface 24 of the ultrasonic transducer 22, thus preventing no-water burning of the ultrasonic waves S1, thus avoiding a technical failure of the ultrasonic transducer 22 caused by the no-water burning.

Figure 21:
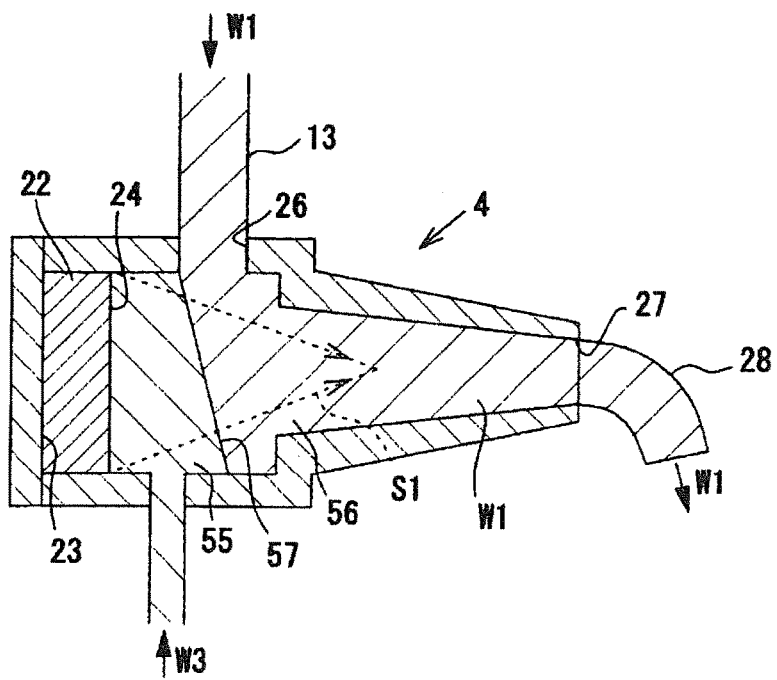
FIG. 21 is an oblique-perspective view of the cleaning device as another embodiment.

As shown in FIG. 21, it is possible to configure the cleaning-device unit 4 such that the inner space of the transducer case 21 is divided into a double-space structure with the medium-holding material 57 supplying the cooling water W3 into the propagating-medium holding space 55. Also, the medium-holding material 57 is provided slantly a little on the vibrating surface 24 of the ultrasonic transducer 22 to keep fully the amount of the cooling water W3 in the propagating-medium holding space 55, thus preventing no-water burning by the ultrasonic waves S1 and the cooling of the ultrasonic transducer 22, thus avoiding a technical failure of the ultrasonic transducer 22 caused by the no-water burning.

Figure 22:
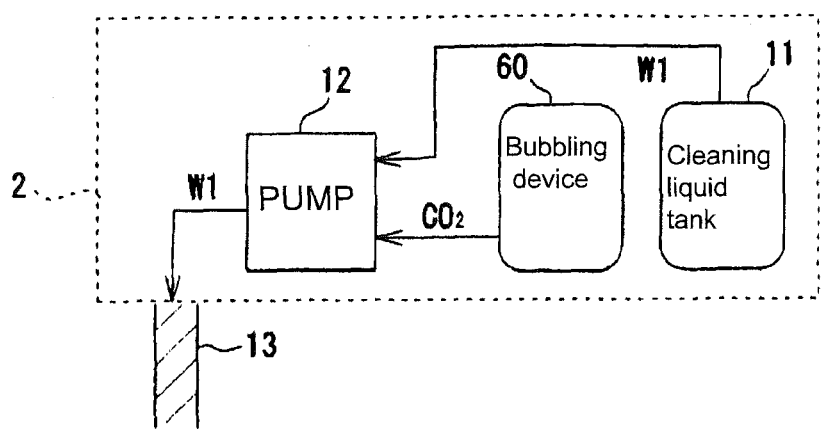
FIG. 22 is a skeleton framework showing the cleaning-liquid supplying device as another embodiment.

As shown in FIG. 22, it is also possible to configure the cleaning-liquid supplying device 2 by further incorporating a bubbling device 60 to bubble the carbon dioxide ($CO_2$) into the cleaning liquid W1. As such, bubbling the carbon dioxide into the cleaning liquid W1 releases the air in the cleaning liquid W1, thereby displacing it to the carbon dioxide. In this case, it is possible to control the OH radical (hydroxyl radical) produced by the emission of the ultrasonic waves S1 into the cleaning liquid W1. In general, when propagating strong ultrasonic waves S1 into the cleaning liquid W1, cavitation occurs, and in the process of the compression and disruption of the cavitation, a strong-reaction field is created. The temperature of the cavitation varies according to the type of gas existing in solution. The cavitation-temperature of a triatomic gas, such as carbon dioxide or the like, is lower than that of a monatomic or diatomic gas. As such, involving the carbon dioxide in the cleaning liquid W1 makes it difficult to produce the OH radical, thus preventing degradation-reaction (chemical reaction) by the OH radical. It is also possible to use a triatomic gas such as laughing gas ($N_2O$) or the like, other than carbon dioxide ($CO_2$), to control the production of the OG radical.

Figure 23:
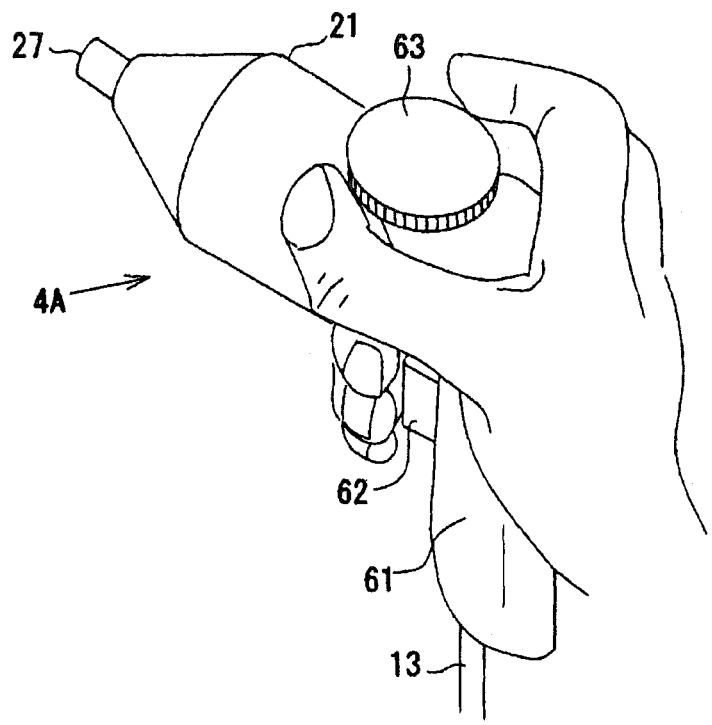
FIG. 23 is an oblique-perspective view of the cleaning device as another embodiment.

Regarding the water-flow ultrasonic oral-cavity cleaning device 1 of the above embodiment, the pen-shaped cleaning-device unit 4 is used. However, it is not limited to it. As shown in FIG. 23, it is also possible to use the cleaning-device unit 4A shaped like a gun. Of the cleaning-device unit 4A, as shown in FIG. 23, a gripper 61 is connected to the rear-end portion of the transducer case 21, and a trigger switch 62 is protrudingly provided on the front side of the gripper 61 for adjusting the input and output of the water-flow. An adjustable dial 63 is provided on the top surface of the gripper 61 for adjusting the volume of the water-flow or the mouth-diameter of the outlet port 27. Using this cleaning-device unit 4A makes it possible to easily adjust the output of the volume or the like of the water-flow, thus making it possible to surely and rapidly clean the oral cavity.

In the above-referenced embodiment, the cross-sectional shape of the outlet port 27 of the transducer case 21 is circular. However, it is possible that it be oval-shaped, thus making it possible to clean the oral-cavity lineally, not at a point. The ultrasonic transducer 22 is ring-shaped, but it is still possible that it be oval-shaped. In this case, the maximum diameter (biggest diameter) should be 50 mm or less. It is also possible to use a rectangular-shaped transducer as the ultrasonic transducer 22. In this case, the shape of the outlet port 27 of the transducer case 21 should be changed to a slit-shape, according to the rectangular shape of the transducer 22. Also, it is preferable to adjust the length of the slit to meet the width of the oral cavity. As such, it is possible to lineally widen the cleaning zone by the cleaning-device unit 4 to clean the oral cavity rapidly. When using the lineal type of cleaning-device unit 4, as above, it is preferable that the value calculated by the arithmetic expression f×D×P is 100 or less under the condition that the frequency is f (kHz), the area of the ultrasonic transducer 22 is S ($m^2$), and the average power supply to the ultrasonic transducer is P (W). As such, it is possible to activate the ultrasonic waves S1 of an acoustic-pressure appropriate for cleaning the treatment portion 42 in the oral cavity, thus efficiently removing the plaque, microorganisms on the oral mucosa, food residue or the like.

The water-flow ultrasonic oral-cavity cleaning device 1 of the above embodiment comprises a special water-suction discharging device 6. However, it is not limited to it. For example, a dental-treatment unit that is equipped with a vacuum device or an electric-pump suction tube can be used. It is also possible to connect the vacuum device or electric-pump suction tube to the joint 39 of the suction nozzle 30 to use it as the water-flow ultrasonic oral-cavity cleaning device. A hospital bed that is equipped with a suction tube can also be used. It is also possible to connect the suction tube to the joint 39 of the suction nozzle 30 to make it the water-flow ultrasonic oral-cavity cleaning device. As such, existing equipment can be used to configure the water-flow ultrasonic oral-cavity cleaning device, thus making it possible to reduce the cost of equipment.

Regarding the water-flow ultrasonic oral-cavity cleaning device 1 of the above embodiment, it is possible to configure the ultrasonic-control device 5 by incorporating an informing means (e.g. a buzzer or a lamp) to inform the user by sound or light of the oscillation (output of the ultrasonic waves S1) of the ultrasonic transducer 22. As such, it is possible to use the water-flow ultrasonic oral-cavity cleaning device 1 efficiently at the clinical site.

Besides the technical ideas of this invention, as described above, the technical ideas as described hereinafter are to be understood.

(1) A water-flow ultrasonic oral-cavity cleaning device, according to any one of the first to the 12th aspects of this invention, is characterized by an adjustment means to adjust the volume of water-flow or the diameter of the outlet port.

(2) A water-flow ultrasonic oral-cavity cleaning device, according to any one of the first to 12th aspects of this invention, is characterized in that the cleaning-liquid discharging means comprises a suction nozzle with a suction port in the vicinity of the outlet port that opens toward the cleaning point which the cleaning liquid hits.

(3) A water-flow ultrasonic oral-cavity cleaning device, according to the eighth aspect of this invention, is characterized in that a lighting means is provided in the center of the ultrasonic transducer, the lighting means being an LED, to emit light to the outlet port.

(4) A water-flow ultrasonic oral-cavity cleaning device, according to the eighth aspect of this invention, is characterized in that the lighting means is provided opposite to the supply port, the lighting means being an LED, to emit light to the inner side of the transducer case.

(5) A water-flow ultrasonic oral-cavity cleaning device, according to any one of the first to 12th aspects of this invention, is characterized by comprising a gripper being connected to the rear-end portion of the transducer case and a switch protrudingly provided on the gripper to control the output of the water-flow.

(6) A water-flow ultrasonic oral-cavity cleaning device to clean an oral cavity ultrasonically by a water-flow of cleaning liquid in which ultrasonic waves are propagated, characterized by a case comprising an ultrasonic transducer to propagate the ultrasonic waves into the cleaning liquid, a transducer mounting part provided at one end of the case to mount the ultrasonic transducer, a supply port to supply the cleaning liquid to a vibrating surface of the ultrasonic transducer, and an outlet port provided on the apical end that is tapered toward the other end against the transducer mounting part to emit water flow of the cleaning liquid, by a cleaning-liquid supplying means that is connected to the supply port to supply the cleaning liquid into the case, and by a cleaning-liquid discharging means to discharge the cleaning liquid which was used in ultrasonically oral-cavity cleaning, whereof the value calculated by the arithmetic expression f×S×P is 100 or less under the condition that the oscillation frequency to activate the ultrasonic transducer is f (kHz), the area of the ultrasonic transducer is S (m$^2$), and the average power supply to the ultrasonic transducer is P (W).

DESCRIPTION OF THE REFERENCE SIGNS

1. Water-flow ultrasonic oral-cavity cleaning device
2. Cleaning-liquid supplying device as a cleaning-liquid supplying means
21. Transducer case
21a. External wall
22. Ultrasonic transducer
23. Transducer mounting part
24. Vibrating surface
26. Supply port
27. Outlet port
28, 28A. Bendable nozzle
29. Reflector
30. Suction nozzle as a cleaning-liquid discharging means
37. Intake port
53. LED as a light-emitting means
60. Bubbling device as a bubbling means
L1. Light
O1. Central axis
S1. Ultrasonic waves
W1. Cleaning liquid
θ1. Angle

The invention claimed is:

1. A water-flow ultrasonic oral-cavity cleaning device to clean an oral cavity ultrasonically by a water-flow of cleaning liquid in which ultrasonic waves are propagated, comprising:
a case comprising an ultrasonic transducer to propagate the ultrasonic waves into the cleaning liquid,
a transducer mounting part provided at one end of the case to mount the ultrasonic transducer,
a supply port to supply the cleaning liquid to a vibrating surface of the ultrasonic transducer,
an outlet port provided on an apical end of the case to emit water flow of the cleaning liquid, the apical end tapered toward an end of the case opposite to the apical end,
a cleaning-liquid supplying device comprising a cleaning-liquid tank that holds the cleaning liquid, a pump that is connected to the cleaning-liquid tank and a supply tube that connects the pump to a supply port of the transducer case, wherein the cleaning liquid is supplied within the case upon activating the pump, and
a cleaning-liquid discharging device comprising suction bodies, each with a suction tube, that are connected to suction ports, wherein used cleaning liquid after ultrasonically cleaning an oral cavity is sucked by the suction bodies and then discharged,
wherein an oscillation frequency to activate the ultrasonic transducer is 100 kHz or more and 3 MHz or less, and a diameter of the ultrasonic transducer is 50 mm or less, and a power supply to the ultrasonic transducer is 100 W or less.

2. The water-flow ultrasonic oral-cavity cleaning device according to claim 1, wherein a bendable nozzle is provided at the outlet port of the case, thus allowing for a change in direction of the water-flow, and the bendable nozzle is bent at an angle of 5 degrees or more to 90 degrees or less with respect to a central axis of the case.

3. The water-flow ultrasonic oral-cavity cleaning device according to claim 2, wherein the bendable nozzle is bent once in the opposite direction to an aperture of an end of the nozzle and then bent again toward the end of the nozzle, with a reflector being provided in the bent portion of the bendable nozzle to reflect the ultrasonic waves in the direction of the aperture.

4. The water-flow ultrasonic oral-cavity cleaning device according to claim 3, wherein the end of the bendable nozzle is set on a central axis of the case.

5. The water-flow ultrasonic oral-cavity cleaning device according to claim 2, wherein an aperture diameter of the bendable nozzle is greater than a wavelength of the ultrasonic waves.

6. The water-flow ultrasonic oral-cavity cleaning device according to claim 1, wherein the cleaning-liquid discharging device comprises an intake port shaped like a fan.

7. The water-flow ultrasonic oral-cavity cleaning device according to claim 1, wherein a light is provided inside the case to emit light to the water-flow.

8. The water-flow ultrasonic oral-cavity cleaning device according to claim 1, wherein a light is provided on each of at least two external-wall portions of the case, each external-wall portion being tapered toward the outlet port so that a cleaning point is indicated where beams of light emitted from each light cross.

9. The water-flow ultrasonic oral-cavity cleaning device according to claim 8, wherein at least one of the lights emits light of a wavelength of 465 nm.

10. The water-flow ultrasonic oral-cavity cleaning device according to claim 1, wherein a bubbling device to bubble carbon-dioxide gas into the cleaning liquid of the cleaning-liquid supplying device is provided.

11. The water-flow ultrasonic oral-cavity cleaning device according to claim 1, wherein the cleaning-liquid discharging device comprises a joint which can be connected to a vacuum device or to an electric-pump suction tube provided on a dental-treatment unit or to an aspiration tube provided on a hospital bed.

12. A water-flow ultrasonic oral-cavity cleaning device to clean an oral cavity ultrasonically by a water-flow of cleaning liquid in which ultrasonic waves are propagated, comprising:
a case comprising an ultrasonic transducer to propagate the ultrasonic waves into the cleaning liquid, a transducer mounting part provided at one end of the case to mount the ultrasonic transducer, a supply port to supply the cleaning liquid to a vibrating surface of the ultrasonic transducer, an outlet port provided on an apical end of the case to emit water flow of the cleaning liquid, the apical end tapered toward an end of the case opposite to the apical end, a cleaning-liquid supplying device comprising a cleaning-liquid tank that holds the cleaning liquid, a pump that is connected to the cleaning-liquid tank and a supply tube that connects the pump to a supply port of the transducer case, wherein the cleaning liquid is supplied within the case upon activating the pump, and a cleaning-liquid discharging device comprising suction bodies, each with a suction tube, that are connected to suction ports, wherein used cleaning liquid after ultrasonically cleaning an oral cavity is sucked by the suction bodies and then discharged, whereof a value calculated by an arithmetic expression $f \times D \times P$ is 500 or less under a condition that an oscillation frequency to activate the ultrasonic transducer is 100 kHz or more, the oscillation frequency is $f$ (kHz), a diameter of the ultrasonic transducer is $D$(m), and an average power supply to the ultrasonic transducer is $P$ (W).

* * * * *